(12) United States Patent
Warnking et al.

(10) Patent No.: US 10,123,903 B2
(45) Date of Patent: Nov. 13, 2018

(54) ABLATION DEVICES AND METHODS WITH ULTRASONIC IMAGING

(75) Inventors: Reinhard Warnking, E. Setauket, NY (US); Yegor Sinelnikov, Port Jefferson, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1349 days.

(21) Appl. No.: 11/665,321

(22) PCT Filed: Oct. 14, 2005

(86) PCT No.: PCT/US2005/037020
§ 371 (c)(1),
(2), (4) Date: Jan. 8, 2008

(87) PCT Pub. No.: WO2006/044662
PCT Pub. Date: Apr. 27, 2006

(65) Prior Publication Data
US 2008/0255449 A1    Oct. 16, 2008

Related U.S. Application Data

(60) Provisional application No. 60/618,944, filed on Oct. 14, 2004.

(51) Int. Cl.
*A61B 8/00* (2006.01)
*A61F 7/02* (2006.01)
(Continued)

(52) U.S. Cl.
CPC .................. *A61F 7/02* (2013.01); *A61B 8/12* (2013.01); *A61B 8/445* (2013.01); *A61B 8/4461* (2013.01);
(Continued)

(58) Field of Classification Search
USPC ....... 600/437, 470, 471, 472, 473, 467, 466, 600/459
See application file for complete search history.

(56) References Cited

U.S. PATENT DOCUMENTS 4,802,487 A * 2/1989 Martin et al. ................ 600/463
4,841,977 A * 6/1989 Griffith .................... A61B 8/12
29/25.35
(Continued)

FOREIGN PATENT DOCUMENTS

WO    00/78230    12/2000

OTHER PUBLICATIONS

Supplementary Partial European Search Report, EP 05 82 3419.

*Primary Examiner* — Joel F Brutus

(57) ABSTRACT

Ablation apparatus such as a catheter (10) carrying an ultrasonic ablation device (20) including an ablation transducer (42) and a balloon reflector structure (22, 24) for directing ultrasonic energy from the ablation transducer into a ring-like ablation region (A) is provided with an imaging ultrasonic transducer (86) mounted on an imaging probe (80) which may be inserted into or through a passageway (18, 65) extending through the catheter and into or through the ablation device to image the ablation region or neighboring regions. Alternatively, the imaging transducer (102, 202) may be mounted within the balloon reflector structure or distal to this structure.

14 Claims, 6 Drawing Sheets

(51) Int. Cl.
*A61B 8/12* (2006.01)
*A61B 17/22* (2006.01)
*A61B 17/00* (2006.01)
*A61B 90/00* (2016.01)

(52) U.S. Cl.
CPC . *A61B 17/2202* (2013.01); *A61B 2017/00243* (2013.01); *A61B 2017/22024* (2013.01); *A61B 2017/22051* (2013.01); *A61B 2017/22058* (2013.01); *A61B 2017/22069* (2013.01); *A61B 2090/3782* (2016.02)

(56) References Cited

U.S. PATENT DOCUMENTS

| | | | |
|---|---|---|---|
| 5,471,988 A * | 12/1995 | Fujio | A61B 8/12 600/439 |
| 5,606,975 A * | 3/1997 | Liang et al. | 600/462 |
| 6,004,269 A | 12/1999 | Crowley et al. | |
| 6,296,619 B1 * | 10/2001 | Brisken et al. | 604/22 |
| 6,394,956 B1 * | 5/2002 | Chandrasekaran et al. | 600/439 |
| 6,457,365 B1 | 10/2002 | Stephens et al. | |
| 6,514,249 B1 * | 2/2003 | Maguire et al. | 606/41 |
| 6,635,054 B2 | 10/2003 | Fjield et al. | |
| 7,837,676 B2 | 11/2010 | Sinelnikov et al. | |
| 2002/0111548 A1 | 8/2002 | Swanson et al. | |
| 2002/0115990 A1 * | 8/2002 | Acker | A61N 7/022 606/27 |
| 2002/0173720 A1 * | 11/2002 | Seo | A61B 8/0833 600/437 |
| 2003/0028210 A1 * | 2/2003 | Boyle | A61F 2/82 606/192 |
| 2003/0229286 A1 | 12/2003 | Lenker | |
| 2004/0176757 A1 | 9/2004 | Sinelnikov et al. | |

* cited by examiner

ABLATION DEVICES AND METHODS WITH ULTRASONIC IMAGING

CROSS-REFERENCE TO RELATED APPLICATIONS

The present application claims the benefit of the filing date of U.S. Provisional Patent Application No. 60/618,944, filed Oct. 14, 2004, the disclosure of which is hereby incorporated by reference herein.

BACKGROUND OF THE INVENTION

The present invention relates to ablation apparatus and methods, including those used in cardiac ablation.

Contraction or "beating" of the heart is controlled by electrical impulses generated at nodes within the heart and transmitted along conductive pathways extending within the wall of the heart. Certain diseases of the heart known as cardiac arrhythmias involve abnormal generation or conduction of the electrical impulses. One such arrhythmia is atrial fibrillation or "AF." Certain cardiac arrhythmias can be treated by deliberately damaging the tissue along a path crossing a route of abnormal conduction, either by surgically cutting the tissue or applying energy or chemicals to the tissue, so as to form scar. The scar blocks the abnormal conduction. For example, in treatment of AF it has been proposed to ablate tissue in a partial or complete loop around a pulmonary vein within the vein itself near the ostium of the vein; within the ostium; or within the wall of the heart surrounding the ostium. It would be desirable to perform such ablation using a catheter-based device which can be advanced into the heart through the patient's circulatory system.

As described in certain embodiments of U.S. Pat. No. 6,635,034, the disclosure of which is hereby incorporated by reference herein, an expansible structure mounted at or near the distal end of a catheter is used as a reflector for directing and focusing ultrasonic waves from an ultrasonic transducer into a region of tissue to be ablated. Certain embodiments according to the '034 patent include an expansible structure incorporating a structural balloon which is inflated with a liquid and a reflector balloon inflated with a gas. The balloons share a common wall. The balloons are configured so that the common wall is generally in the form of a surface of revolution of a parabolic curve about a central axis. Because the liquid in the structural balloon and the gas in the reflector balloon have substantially different acoustic impedances, the interface between the balloons at the common wall is a nearly perfect reflector for ultrasonic waves. Ultrasonic waves are emitted from a small cylindrical transducer within the structural balloon, coaxial with the aforementioned reflector. These waves pass radially outwardly from the emitter to the reflector. The reflector redirects the ultrasonic waves and focuses them into a ring-like ablation region encircling the central axis of the emitter and balloons. This ablation region is just forward of the structural balloon. Thus, the ultrasonic waves will ablate tissue in a region encircling the central axis or forward-to-rearward axis of the balloon structure. This ring-like region is disposed at a known location relative to the balloon structure.

This arrangement can be used, for example, to treat atrial fibrillation by ablating a circular region of myocardial tissue encircling the ostium of a pulmonary vein. The ablated tissue forms a barrier to abnormal electrical impulses which can be transmitted along the pulmonary veins and, thus, isolates the myocardial tissue of the atrium from the abnormal impulses. To provide effective treatment in this mode of operation, the ring-like focal region should encircle the ostium and should lie in the myocardial tissue of the heart wall.

It is desirable to maintain the expansible structure in a predetermined configuration and, in particular, to keep the distal end of the structural balloon coaxial with the proximal end of the structural balloon and with the reflector and transducer. The expansible structure may be provided with a distal engagement element mechanically connected to the distal end of the structural balloon and with a proximal engagement element mechanically connected to the transducer and to the proximal end of the structural balloon. These elements engage one another to reinforce the expansible structure when the structural balloon is inflated, but at least partially disengage from one another when the structural balloon is deflated, so that the deflated, collapsed structure is flexible and can be threaded through the vascular system into the heart. Additionally, the expansible structure desirably is provided with a bore connected to a lumen of the catheter so that the expansible structure and the catheter cooperative define a continuous passageway extending from adjacent the proximal end of the catheter to the distal side of the expansible structure. This passageway can be used to introduce an X-ray or other contrast agent during the procedure, so the position of the expansible structure relative to anatomical features of the heart may be determined by imaging. Moreover, the catheter desirably is steerable so that a portion of the catheter adjacent the distal end can be selectively bent by the physician, so as to reposition the expansible structure. These features are further described in certain embodiments of co-pending, commonly assigned U.S. patent application Ser. No. 10/783,310, filed Feb. 20, 2004 ("the '310 application"); PCT International Application No. PCT/US04/05197; and U.S. Published Patent Application 20040054362A1, filed Sep. 16, 2002; as well as in co-pending, commonly assigned U.S. patent application Ser. No. 10/635,170, filed Aug. 6, 2003 and PCT International Application No. PCT/US03/28578, filed Sep. 12, 2003. The disclosures of all of the aforementioned applications and publications are hereby incorporated by reference herein.

Despite all of these advances in the art, still further improvement would be desirable. In particular, it would be desirable to provide apparatus and methods for ablation which allow the physician to acquire information about anatomical structures of the heart and surrounding tissues. Such information can be used in positioning the ablation device. For example, where structures other than myocardial tissue must remain intact after the ablation procedure, such information allows the physician to position the ablation device so as to avoid ablating these structures. Conversely, where structures such as certain nerve bundles are to be ablated, such information allows the physician to more accurately position the ablation device for greater certainty of ablating these structures.

SUMMARY OF THE INVENTION

Certain aspects of the present invention address these needs. One aspect of the invention provides ablation apparatus. The apparatus according to this aspect of the invention preferably incorporates a structure which includes a catheter having a proximal end and a distal end. The structure also includes an expansible ablation device mounted to the catheter adjacent the distal end. The ablation device has an expanded condition and a collapsed condition. Most preferably, a continuous passageway extends from adjacent the proximal end of the catheter to the ablation device.

The apparatus according to this aspect of the invention most preferably includes an ultrasonic imaging probe. The imaging probe includes at least one imaging transducer, and is adapted to image structures in the vicinity of the imaging transducer. Most preferably, the probe has an operative condition in which the probe is positioned in the passageway and the imaging transducer is disposed adjacent the ablation device. However, the probe most preferably is removable from the passageway so that the passageway can be used for other purposes. Typically, the structure defines a port distal to the ablation device and the passageway extends to the port. The imaging probe may be movable to an extended position in which the imaging probe projects through the port so that the transducer is disposed distal to the ablation device. The ablation device, in its expanded condition, desirably has an axis extending generally proximally and distally. The ablation device may be operative to apply ablation energy in a loop-like ablation region encircling the axis. The port may be disposed adjacent the axis of the ablation device, so that the imaging probe may be extended through the passageway and out of the port and rotated to acquire an image of a loop-like region surrounding the axis. In some cases, an image acquired in this manner will show a region of tissue distal to the ablation region. Desirably, the imaging probe is movable to an interior operating position in which the imaging transducer is disposed inside of said expansible ablation device. When the imaging probe is in this interior operating position, it can be operated to image tissue surrounding the ablation device, and most preferably tissue in the ablation region.

Apparatus according to a further aspect of the invention includes a catheter having a proximal end and a distal end, and also includes an expansible ablation device mounted to the catheter adjacent its distal end. Here again, the ablation device has an expanded condition and a collapsed condition. In the expanded condition, the ablation device has an axis extending generally proximally and distally. The ablation device in this aspect of the invention includes an ultrasonic ablation transducer disposed adjacent the axis and a reflector extending around said axis. The reflector is operative to direct ultrasonic waves emitted by the ablation transducer generally distally into a loop-like ablation region encircling the axis. The apparatus according to this aspect of the invention also includes an ultrasonic imaging transducer separate from the ultrasonic ablation transducer. The imaging transducer being is also disposed adjacent the axis when the ablation device is in its expanded condition. The imaging transducer is operative to receive return waves reflected by said reflector. For example, the imaging transducer will receive return waves from the ablation region, and can be used to image the ablation region.

Apparatus according to yet another aspect of the invention includes an expansible ablation device incorporating a balloon structure. An ablation transducer is mounted within the balloon structure. The balloon structure defines a reflector extending around an axis when said balloon structure is in an inflated condition. The reflector is operative to direct ultrasonic waves emitted by said transducer generally distally into a loop-like ablation region encircling the axis. An ultrasonic imaging transducer is mounted to said balloon structure distal to said ablation transducer as, for example, on a fitting at the distal end of the balloon structure. Here again, the imaging transducer can be used to image the ablation region.

DESCRIPTION OF THE PREFERRED EMBODIMENTS

Figure 1:
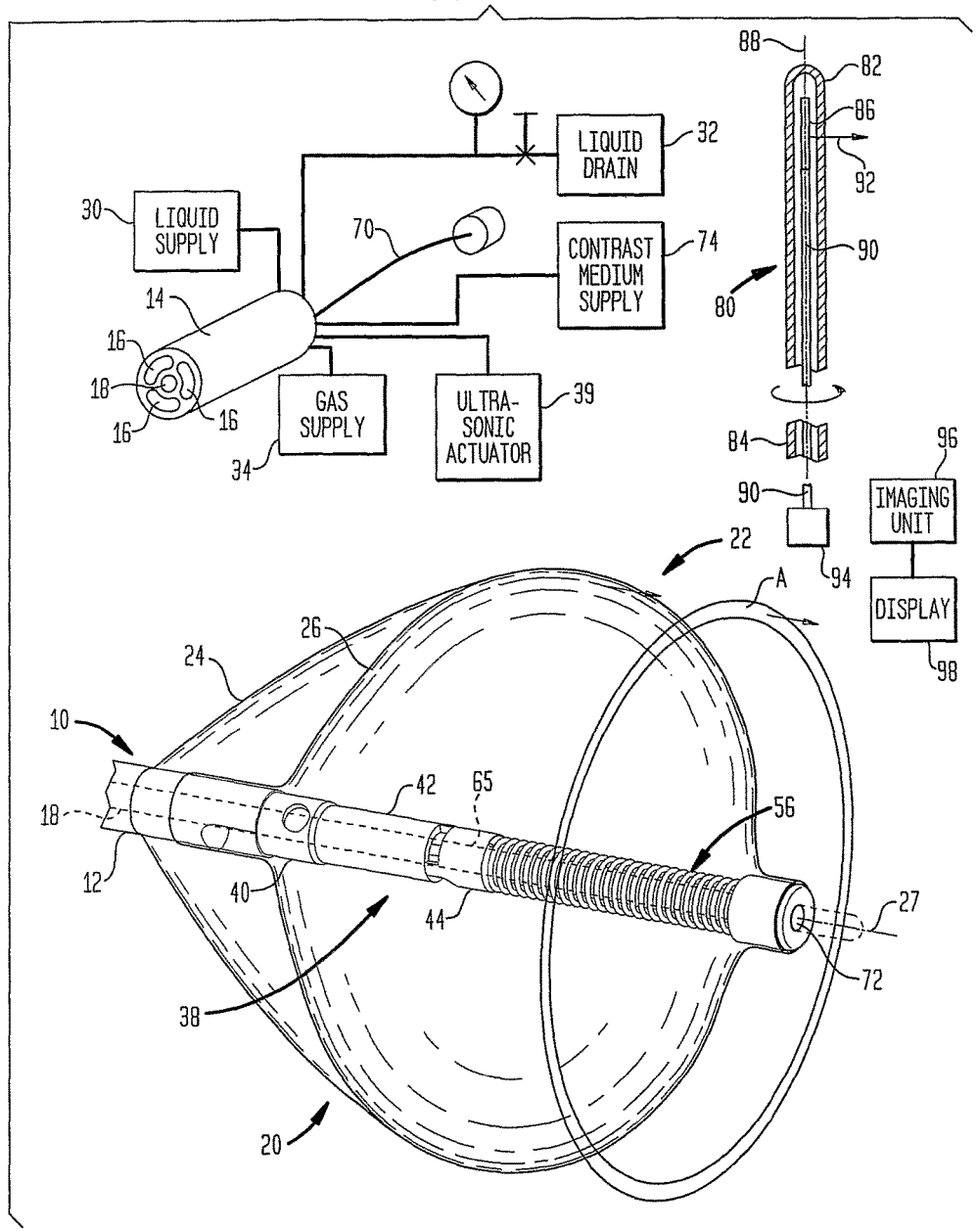
FIG. 1 is a diagrammatic, partially perspective view of apparatus according to one embodiment of the present invention.
Figure 2:
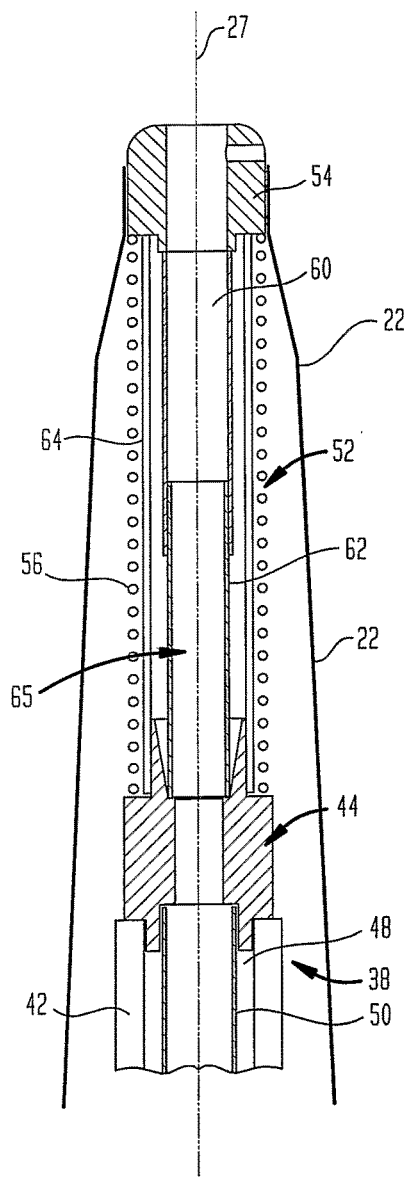
FIG. 2 is a fragmentary, diagrammatic sectional view depicting a portion of the apparatus of FIG. 1.

Apparatus in accordance with one embodiment of the invention includes a catheter 10 (FIG. 1) having a distal end 12 and a proximal end 14. The catheter incorporates several peripheral lumens 16 and a central lumen 18, these lumens extending between the proximal and distal ends of the catheter. An expansible ablation device 20 is mounted to the distal end 12 of the catheter. The expansible inflation device incorporates a structural balloon 22 and a reflector balloon 24 having a common wall 26 between them. In the inflated, expanded condition illustrated in FIG. 1, balloons 24 and 22 are substantially symmetrical about a central axis 27. The common wall 26 between these balloons forms a reflector in the form of a surface of revolution about the central axis 27. The interior of structural balloon 22 is connected through two lumens 16 to a liquid supply unit 30 and drain 32, so that the structural balloon may be filled with a liquid. The interior of reflector balloon 24 is connected to a gas supply apparatus 34 through another lumen of the catheter, so that this balloon may be inflated with a gas such as carbon dioxide. A transducer structure 38 is mounted inside structural balloon 22. This transducer structure incorporates a proximal end fitting 40 physically connected to the distal end 12 of the catheter, a therapeutic ultrasound transducer 42 mounted to the proximal end fitting and a distal end fitting 44 mounted to the transducer. Transducer 42 is generally hollow and tubular, and defines an interior space 48 (FIG. 2). A central tube 50 extends through space 48. This tube 50 communicates with the central lumen 18 (FIG. 1) of the catheter. The features of the transducer structure are substantially symmetrical about the central axis 27 of the balloon structure. For example, cylindrical transducer 42 is coaxial with the central axis 27.

The expansible ablation device also includes a reinforcing and collapsing structure 52. This structure incorporates a distal end piece 54. The distal end of structural balloon 22 is fastened to distal end piece 54. A coil spring 56 is mounted between distal end piece 54 and the distal fitting 44 of transducer unit 38. A distal engagement element in the form of a reinforcing tube 60 is connected to distal end piece 54, whereas a proximal engagement element or reinforcing tube 62 is mounted to the distal fitting 44 of the transducer assembly. The proximal reinforcing tube 62 is telescopically received in the distal reinforcing tube 60. A distensible tube 64 also extends between the distal end piece 54 and the transducer assembly.

A pull wire 70 is connected to the transducer assembly through one of the lumens of the catheter. The connection between the pull wire and the proximal fitting 40 of the transducer assembly is displaced from the central axis 27 of the ablation device. The features of the transducer structure are substantially symmetrical about the central axis 27 of the balloon structure. For example, cylindrical transducer 42 is coaxial with the central axis 27.

Figure 3:
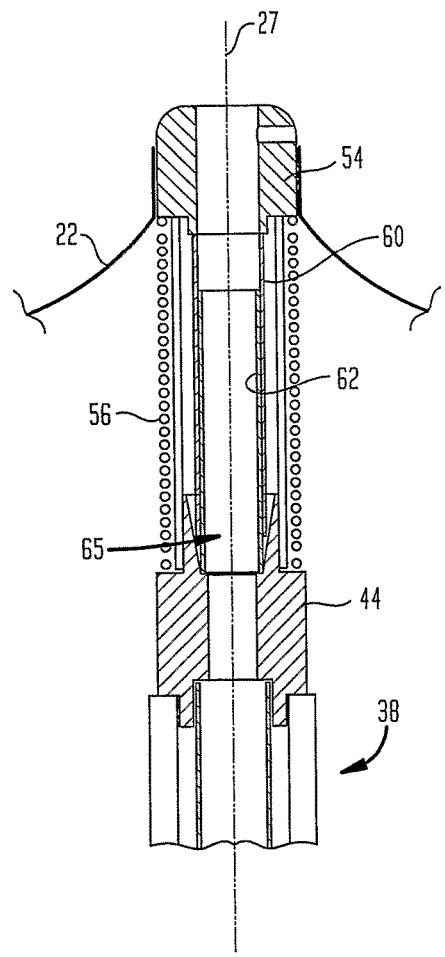
FIG. 3 is a view similar to FIG. 1 depicting the same portion of the apparatus in a different operating condition.

In the deflated, collapsed condition shown in FIG. 2, coil spring 56 is extended and tubes 60 and 62 are in a disengaged condition, wherein only a minor portion of tube 62 is disposed inside tube 60. In this condition, balloons 22 and 24 (FIG. 1) are collapsed and twisted about central axis 27. In this condition, the ablation device 20 is relatively flexible in directions transverse to the central axis 27, so that the catheter, with the ablation device thereon, may be advanced into the vascular system so as to position the ablation device inside a chamber of the heart. When the ablation device is inside the chamber of the heart, the ablation device is brought to the expanded, inflated condition of FIGS. 1 and 3 by inflating the balloons 24 and 22. During inflation, balloon 22 untwists, expands radially and shortens axially, so that distal end piece 54 is moved proximally towards transducer assembly 38. Spring 56 is compressed between the distal end piece and the distal fitting 44 of the transducer assembly. Spring 56 is also twisted about axis 27. Also, during inflation and expansion, distal reinforcing tube 60 moves proximally to the condition illustrated in FIG. 3, in which it encompasses most or all of proximal reinforcing tube 62. In this condition, the reinforcing tubes are substantially more rigid. Therefore, the reinforcing tubes cooperatively reinforce the balloon structure and limit displacement of the distal end of balloon 22 relative to the proximal end of the balloon and relative to transducer assembly 38. During deflation, these actions are reversed; spring 56 forces the distal end piece 54 distally, away from the proximal end and away from the transducer assembly, thereby helping to collapse the balloon. At the same time, the spring twists the distal end piece 54 about axis 27, thereby twisting the balloon about the axis, which further aids in collapse of the balloon.

Reinforcing tubes 60 and 62 of the reinforcing structure communicate with the central tube 48 of the transducer assembly, and thus define a bore 65 extending through the ablation device 20. Bore 65 communicates with the central lumen 18 (FIG. 1) of the catheter. These structures cooperatively define a continuous passageway extending from the proximal end 14 of the catheter, through the catheter and through the ablation device 20, to a port 72 on distal fitting 54. This passageway is open at all times, whether the ablation device is in the collapsed condition or in the expanded condition. As best seen in FIG. 1, port 72 lies on the distal side of ablation device 20. As discussed in the aforementioned applications and publications, elements such as a guide wire for use in threading may be advanced through this passageway. Also, a contrast medium may be introduced through this passageway by temporarily connecting a contrast medium supply 74 to the central lumen.

While the ablation device is in the inflated expanded condition, therapeutic transducer 42 of the transducer assembly 38 may be actuated to emit ultrasonic waves by actuator 39. The ultrasonic waves emitted by transducer 38 will be reflected forwardly or distally by reflector surface 26 of the balloon structure, and will be focused into a relatively narrow, ring-like or loop-like ablation region A (FIG. 1). This ablation region encircles axis 27 and lies in a known, predetermined spatial relationship to the ablation device, just forward of the structural balloon 22. The entire ablation device 20, and hence axis 27, can be turned by pulling on pull wire 70 to bend the distal region of the catheter.

The foregoing features may be similar to those disclosed in the '310 application. However, in the apparatus of FIGS. 1-4, the reinforcing structure desirably is formed from materials which are substantially transparent to ultrasonic energy. For example, tubes 60 and 62, and distensible tubes 64 and spring 56, desirably are formed from materials having an acoustic impedance close to that of aqueous liquids such as certain polymers such as epoxies, polyether block amides sold under the registered trademark PEBAX, polycarbonate, PET and fluouropolymers. Distal fitting 54 also may be formed from such materials.

Figure 4:
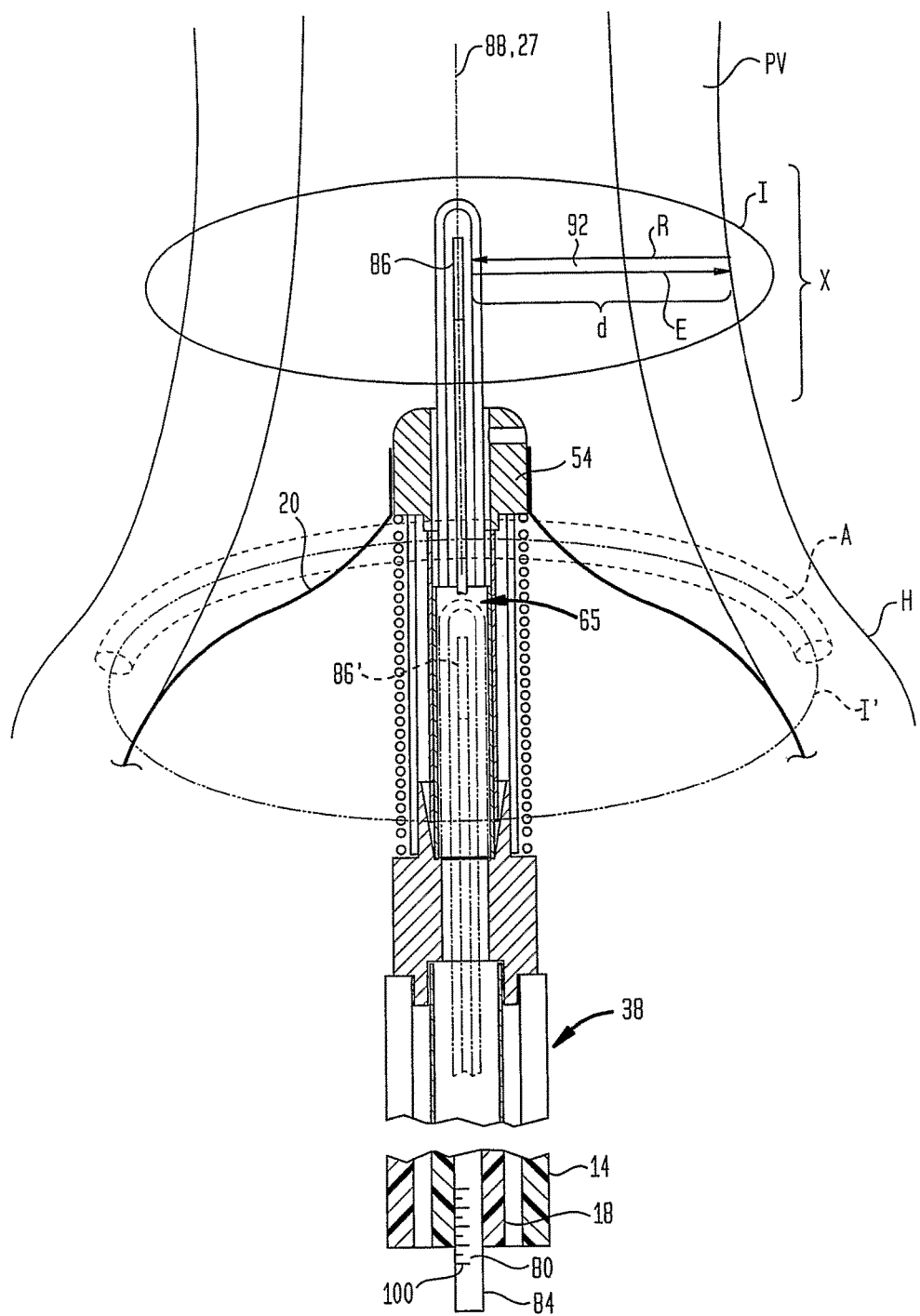
FIG. 4 is a fragmentary, diagrammatic sectional view depicting portions of the apparatus of FIGS. 1-3 in conjunction with anatomical structures during operation.

The apparatus additionally includes an imaging probe 80, shown in FIGS. 1 and 4. The imaging probe includes a casing having a distal end 82 and a proximal end 84. An imaging transducer 86 is mounted within the casing at or adjacent the proximal end. Imaging transducer 86 is rotatable about the central axis 88 of the probe. A driveshaft 90 extends between the proximal and distal ends of the imaging probe. Transducer 86 is arranged to emit and receive signals along an axis 92 transverse to the axis 88 of the probe. By rotating driveshaft 90, the transducer 86 and, hence, axis 92 may be turned around the axis 88 of the probe. A manual or motor-actuated drive 94 is linked to the proximal end of the driveshaft for rotating or pivoting the driveshaft and imaging transducer. The imaging transducer is electrically connected through leads (not shown) to an imaging unit 96. The imaging unit 96 includes a drive circuit (not shown) for actuating transducer 86 to emit ultrasonic waves and a receiver unit adapted to detect electrical signals produced by transducer 86 in response to ultrasonic waves impinging on the transducer. The imaging unit is arranged to actuate transducer 86 with pulses of drive signals and to receive the electrical signals generated by the transducer at a selected time after emission of a pulse. The imaging unit includes a control circuit operable to select the interval between emission and reception, referred to herein as the "delay time." Thus, the transducer 86 will emit signals E and receive signals R, reflected from anatomical features at a selected distance D, such distance depending upon the delay time. As best appreciated with reference to FIG. 4, an annular or arcuate imaging region I can be imaged by maintaining a substantially constant distance D or, i.e., a constant delay time, and rotating or pivoting transducer 86 about the axis 88 of the imaging probe. The imaging unit 96 is linked to display unit 98, so that the resulting image can be displayed and viewed.

The features of imaging probe 80 and associated equipment may be substantially similar to those used in conventional intravascular ultrasound imaging equipment. For example, imaging probe 80 may be an intravascular ultrasound imaging probe of the type sold under the designation Atlantis Coronary Imaging Catheter by the Boston Scientific Company. The imaging unit 96 may be of the type sold under the designation Galaxy Imaging System by the Boston Scientific Company.

In use, imaging probe 80 may be inserted through the continuous passageway defined by lumen 18 and the bore 65 of the ablation device 20, so that the axis 88 of the imaging probe is coaxial with the axis 27 of the ablation device. This may be performed while the ablation device is in an expanded condition, as seen in FIG. 4. By moving the imaging probe axially with respect to the ablation device, annular or arcuate regions I at selected axial positions relative to the ablation device may be imaged. In the advanced, projecting condition illustrated in solid lines in FIG. 4, the imaging transducer 86 of the imaging probe is disposed just forward of distal fitting 54 and just forward of the structural balloon 22, so that when the transducer is rotated and actuated, it will image a region I coaxial with the central axis 27 of the ablation transducer, but forward or distal to the ablation region A. The imaging probe can be moved within the bore 65 of the ablation device so as to move the imaging region I. In the interior operating position illustrated in broken lines in FIG. 4, the imaging probe is partially retracted so that the transducer lies at position 86', and the transducer will image a region I' at the same axial location as the ablation region A. As set forth above, the radius of the imaged region I or I' can be varied by adjusting the imaging unit to vary the delay time between pulse emission and reception. In the condition shown in broken lines, the imaged region I' has the same diameter as the ablation region A, and hence the image seen on display unit 98 (FIG. 1) represents tissues within the ablation region. When the imaging catheter is in this interior operating position, ultrasonic waves emitted by the imaging transducer pass outwardly through the reinforcing structure 52 and through the liquid contained in structural balloon 20, and also pass through the wall of the structural balloon itself. The imaging probe 80 can be moved over a range of axial positions, including positions between the positions depicted and positions distal to and proximal to the positions depicted, so as to acquire images at a corresponding range of axial positions. Thus, the image may include data representing tissue structures at various axial and radial locations.

In order for the physician to interpret the images, it is desirable for the physician to know the location of the imaged region I relative to the ablation region A. The proximal end 84 (FIG. 1) of the imaging catheter may have marks or graduations 100 (FIG. 4) thereon, so that the physician can gauge the axial position of the imaging catheter by monitoring which graduation aligns with the proximal end 14 of catheter 10. Alternatively or additionally, mechanical interconnections may be provided between imaging probe 80 and the catheter 10 carrying the ablation device 20 for positioning the imaging probe at one or more preselected axial positions. For example, the proximal end 84 of the probe may be provided with a fixed or adjustable shoulder (not shown) which can be engaged with a fixed or adjustable stop (not shown) on the proximal end 14 of the catheter. In another alternative, electrical sensing devices (not shown) may be provided for determining the axial position of the imaging probe relative to the catheter. Certain known imaging systems, such as the system now or previously sold by the Endosonics Corporation of Rancho Cordova, Calif. under the designation Trak Back, automatically move an intravascular imaging probe axially during image data acquisition so as to form a three-dimensional image of a blood vessel and surrounding structures. Systems of this nature can be employed in the present invention.

In a method according to one aspect of the present invention, the physician may position the ablation device 20 adjacent the ostium of a pulmonary vein PV so as to align the ablation region A with a portion of the heart wall H surrounding the ostium. This alignment may be checked, for example, by introduction of contrast medium through the passageway. Once the device is positioned, the physician may insert the imaging probe 80 through the continuous passageway defined by the central bore 18 of the catheter and the bore 65 of the ablation device and position the imaging probe using graduations 100. The physician may acquire images at various locations. In the particular patient depicted schematically in FIG. 4, a feature X which should not be ablated (as, for example, a coronary artery, nerve or the like) extends in the vicinity of the ablation region. If the image of region I', coincident with the ablation region, shows feature X, this indicates that feature X will be ablated if the ablation transducer 38 is actuated in this position. The physician may choose to move the ablation device to another location as, for example, by tilting the axis 27 of the ablation device, or by retracting or advancing the ablation device axially. The physician may reconfirm that he has successfully avoided feature X by taking a further image. After ablation, the physician may repeat the imaging step or steps to confirm the extent of the ablation.

Apparatus according to a further embodiment of the invention (FIGS. 5 and 6) includes a catheter 110 and expansible ablation device 120 similar to those discussed above with reference to FIGS. 1-4. However, in this embodiment, the expansible ablation device incorporates an imaging transducer array 102 as a part of the transducer assembly 138. The imaging transducer array 102 incorporates a set of individual transducer elements 104 mounted in a circular pattern around the central axis 127 of the ablation device, just proximal to cylindrical therapeutic ultrasound transducer 142. The transducer elements 104 of array 102 face outwardly, away from axis 127, and hence face toward the reflector 126 defined by the common wall between the balloons of the ablation device. Here again, the therapeutic ultrasound transducer 138 is connected to an ultrasonic actuator 139 by conductors (not shown) extending within catheter 110. The individual elements 104 of imaging array 102 are connected by similar conductors to an imaging receiver 106 arranged to acquire an individual signal from each element. Ultrasonic actuator 139 in this embodiment is arranged so that it can be selectively operated to actuate therapeutic transducer 142 in a pulse mode. The actuator is linked to the imaging receiver so that the imaging receiver can be operated to receive signals from each element only within selected receive intervals commencing at a predetermined delay time after termination of a pulse from actuator 139. The imaging receiver is arranged to reconstruct an image of a ring-like region based on individual signals received from the individual elements 104 of array 102. In a simple reconstruction process, there may be a direct one-to-one association between a single element 104 and a single sector of the ring-like image, so that the brightness or other value of the sector in the image is directly proportional to the amplitude of signals generated by the associated element 104 of the array during a receive interval. Other, more complex reconstruction algorithms may be employed. For example, the value of a particular sector may be proportional to a weighted sum of the amplitudes of signals received by a plurality of elements 104. Alternatively, the value of a particular sector may be proportional to a weighted sum of the signals received by a plurality of elements with some of these signals delayed relative to others. For example, the value of a sector aligned with element 104*a* (FIG. 5) may be proportional to the amplitude of a combined signal obtained by adding a delayed replica of the signal received by element 104*a* to the signals received by neighboring elements 104*b* and 104*c*. The delay compensates for the shorter signal path length from the sector being imaged to element 104*a*. A display 198 is associated with receiver 106 for displaying a visible representation of the reconstructed image.

Figure 5:
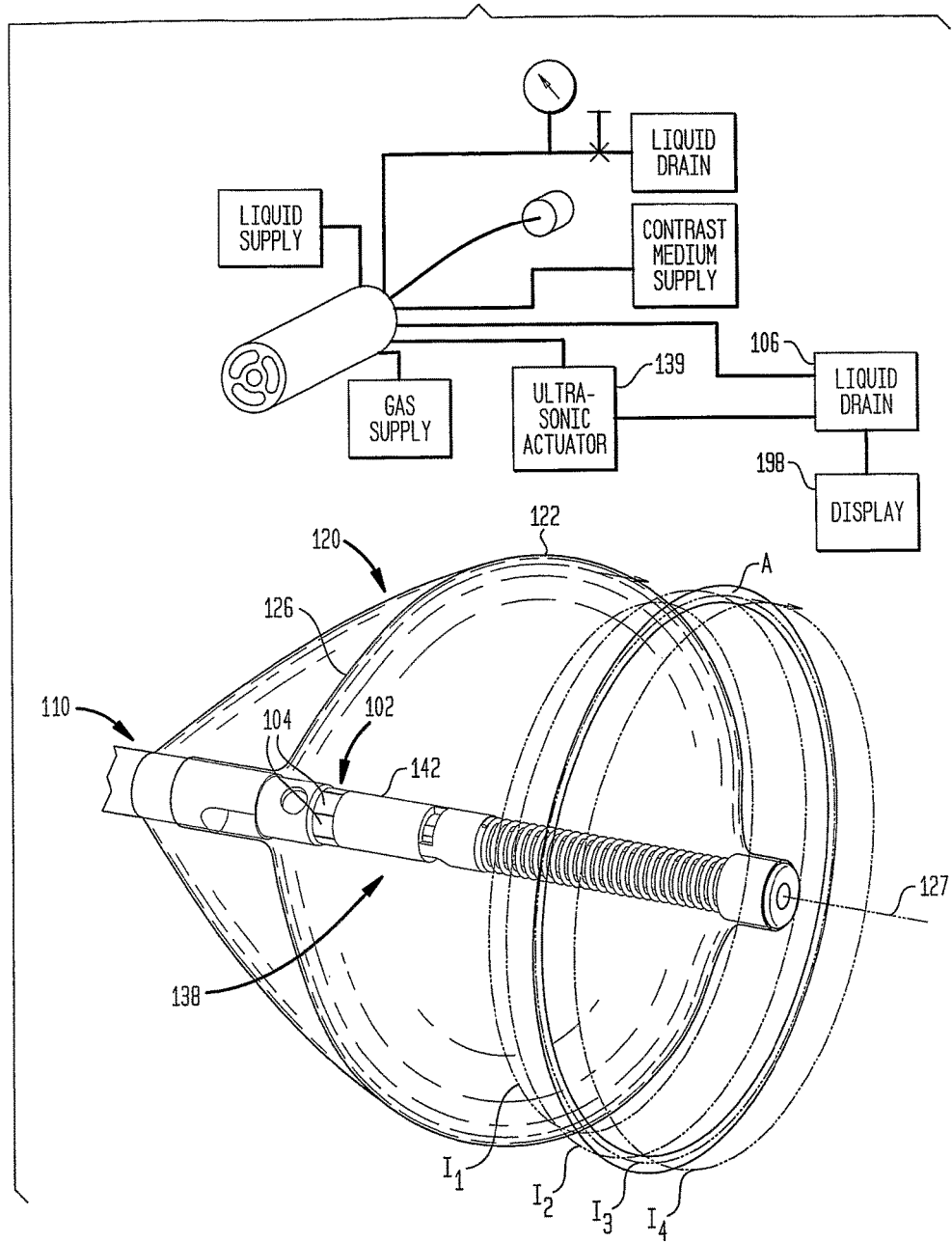
FIG. 5 is a view similar to FIG. 1 but depicting apparatus in accordance with a further embodiment of the invention.
Figure 6:
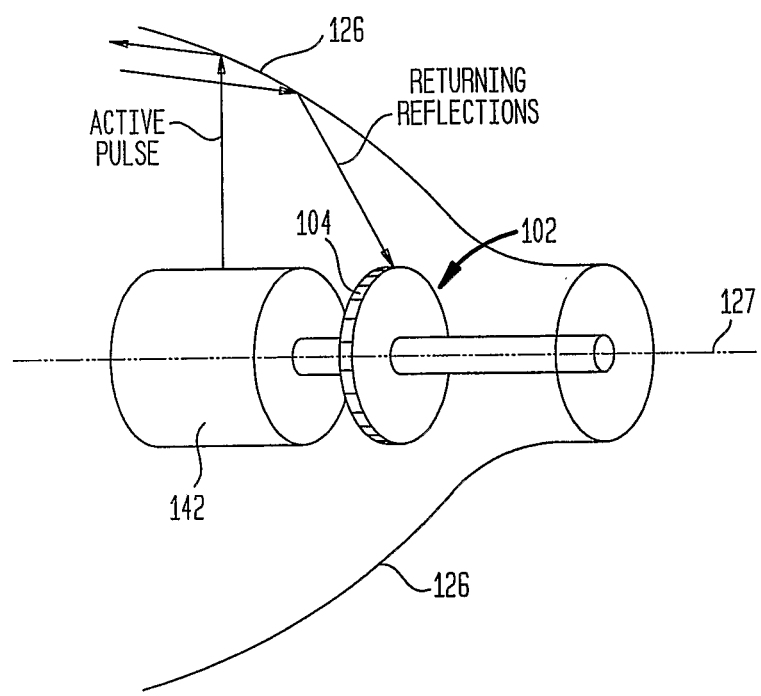
FIG. 6 is a diagrammatic view depicting certain portions of the apparatus of FIG. 5.

In operation, the ablation device is placed in the heart as discussed above. In an imaging operation, actuator 139 sends a brief pulse of energy to therapeutic 142, which emits a relatively low power pulse of ultrasonic energy, referred to herein as the "imaging pulse." The waves in this imaging pulse pass radially outwardly to reflector 126 of the balloon structure. These waves are directed and focused forwardly, toward the ablation region A (FIG. 5). After a predetermined delay time, imaging receiver 106 detects signals representing reflections returned to the elements 104 of imaging array 102. These reflected waves will be the waves reflected at reflective interface 126 (FIG. 6). Stated another way, reflector 126 acts as a reciprocal focusing element, so that waves reflected from the region forward of reflector 126 and will be focused onto the imaging array 102. The delay time between emission of the imaging pulse by therapeutic transducer 142 and reception by array 102 can be varied. Such variation will move the imaged region axially. Where the delay time is a time $T_1$, shorter than the round-trip time for propagation of waves to and from the ablation region A via reflector 126, the imaged region will be a region $I_1$ disposed proximal to the ablation region. This imaged region may lie entirely inside of the structural balloon 122. As the interior of the structural balloon is filled with an aqueous liquid, there will be very little reflection from the imaged region $I_1$, and hence, the signal from all of transducers 104 will be a low-level signal. The aqueous liquid in structural balloon 122 has uniform properties. Assuming that the therapeutic transducer 142 emits uniformly in all radial directions, and the ultrasonic waves impinging on all of the transducer elements 104 at this stage will be uniform. Differences among the signals from the various imaging transducer elements at this stage of operation indicate non-uniform sensitivities of the various imaging transducer elements 104, non-uniform emission from the therapeutic transducer 142 in different radial directions, or some combination of both of these phenomena. Calibration factors can be calculated based on the differences in imaging transducer signals observed at this stage of operation and applied to signals observed at subsequent stages to compensate for these phenomena. To provide larger signals at this stage of operation, the delay time can be selected so that imaged region $I_1$ lies at the distal wall of the structural balloon. The slight mismatch in acoustic impedance between the aqueous liquid in the balloon and the wall will increase the amplitude of the reflected ultrasonic waves and hence will provide larger signals for use in the calibration process.

Also, the signals detected by the imaging transducer provide a measure of the power emitted by the therapeutic transducer. The power output from the therapeutic transducer can be optimized by varying the frequency of the excitation signals applied to the therapeutic transducer and manually or automatically monitoring the emitted power using the signals from the therapeutic transducer so as to select a drive frequency which gives maximum power output from the therapeutic transducer.

As the delay time is progressively increased, the imaged region moves distally, so that at a delay time $T_2$, slightly greater than $T_1$, the imaged region $I_2$ lies just forward of the structural balloon 122 but slightly proximal to ablation region A. A strong, uniform reflection observed on all transducer elements 104, and hence, all segments of the image formed at delay time $T_2$ indicates that imaged region $I_2$ lies directly on the surface of the heart wall at all positions around the circumference of the imaged region. This indicates that the device is aligned as desired to form a continuous loop-like lesion, with the axis 127 of the ablation device generally perpendicular to the heart wall, and with the ablation region A lying slightly beyond the inner surface of the heart wall, and hence, inside the myocardial tissue. Conversely, a weak or non-existent signal indicates that the device is not positioned in this manner. A non-uniform signal typically indicates that blood is present at some portion of the imaged region $I_2$, either because there is a large gap between the surface of the structural balloon and the surface of the heart wall, or because there is a blood vessel extending within the heart wall at or near the depth of the imaged region $I_2$. With further increases in the delay time, the imaged region moves to position $I_3$, coincident with the ablation region. With still further increases in the delay time, the imaged region can move to position $I_4$, distal to the ablation region. A non-uniform signal observed at position $I_3$ or $I_4$ may indicate, for example, that a portion of the imaged region $I_3$ or $I_4$ lies outside of a region occupied by uniform myocardial tissue. This can indicate the presence of a blood vessel at the imaged region, or may indicate that the imaged region extends outside of the heart wall. This can indicate that the ablation region lies too close to the outer surface of the heart wall. When the ablation device is properly positioned relative to the heart, therapeutic transducer 142 is operated in a high-power continuous wave mode to deliver a dose of ultrasonic energy to the ablation region A sufficient to ablate the tissue in this region. Because the axial location of the imaged region is a known function of the delay time and because the axial location of the ablation region is fixed relative to the ablation device, the spatial relationship between the imaged region and the ablation region is always known or determinable from the duration of the delay time used in creating a particular image.

It is not essential that the array provide what would normally be regarded as a sharp, well-defined image. The system typically will provide good spatial resolution in the axial direction, and will also have some resolution in the circumferential direction around axis 127. Radial resolution in the direction perpendicular to axis 127, can be provided by using multiple an imaging transducer having multiple rows of transducer elements at different axial positions relative to the reflector 126 and therapeutic transducer 142, or by shifting the imaging transducer axially relative to the therapeutic transducer and reflector and acquiring data at plural axial positions of the imaging transducer. However, so long as the overall signal strength in the reflected image can be detected, the image still can provide valuable information. In a variant, the imaging transducer array 104 may be replaced by a single cylindrical transducer which would provide an image consisting of only a single value for the entire ring-like region imaged. In another variant, the imaging transducer may include only one element, or a few elements, and may be arranged to rotate around axis 127 in a controlled manner while repeated pulses are applied by therapeutic transducer 142. In this arrangement, the information acquired by the imaging transducer at different rotational positions corresponds to the information acquired by different transducer elements 104 at different circumferential locations in the embodiment of FIG. 5.

In a further variant, therapeutic transducer 142 may include an array of elements disposed around the circumference of the transducer, and hence, around axis 127. Image data acquired using the imaging transducer array or the other imaging modalities discussed herein may be used to select different actuation intensities or actuation durations for the different elements of the therapeutic transducer. Alternatively or additionally, the different elements of the therapeutic transducer may be actuated at different times during an imaging operation so as to image only a portion of the ring-like imaging region.

In yet another variant, the therapeutic transducer can be used as an imaging transducer as well. In a further variant, the imaging transducer may be actuated to emit ultrasonic waves as well as to receive them. Also, the imaging transducer can include more than one row of elements disposed circumferentially around the axis. These rows need not be contiguous with one another. For example, an imaging transducer can include one row disposed proximal to the therapeutic transducer, and another row disposed distal to the therapeutic transducer. In this case, delay time or phase relationships between signals from elements of the two rows may be used to enhance the resolution achievable by the transducer. Stated another way, adding elements to extend the transducer axially can increase the numerical aperture of the transducer.

Figure 7:
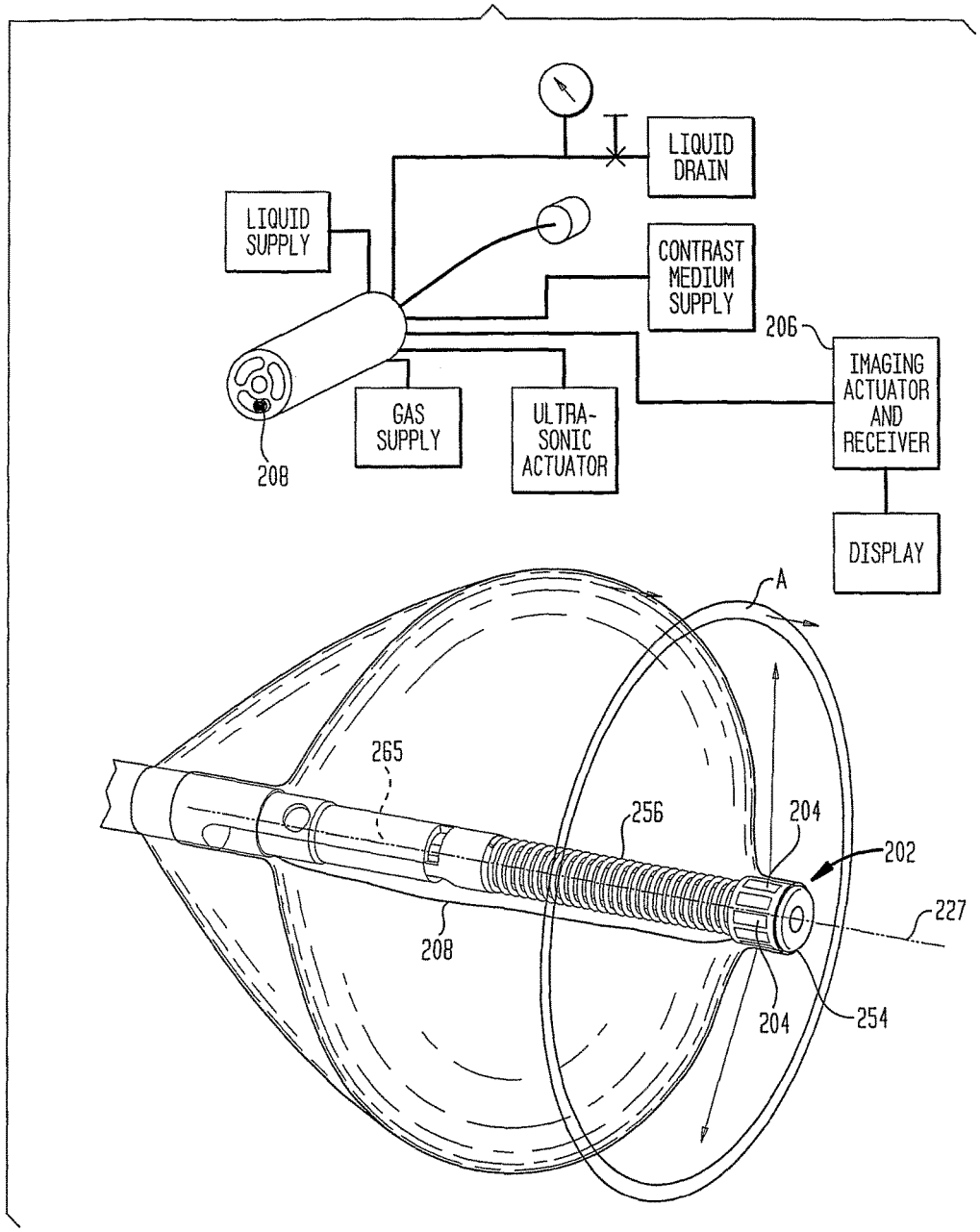
FIG. 7 is a view similar to FIG. 1 depicting apparatus according to yet another embodiment of the invention.

Apparatus according to yet another embodiment of the present invention (FIG. 7) incorporates an imaging transducer 202 in the form of an array of imaging transducer elements 204 extending circumferentially around axis 227. This array 202 is disposed on the distal fitting 254 of the expansible ablation device. This array of transducer elements is connected to an imaging actuator and receiver 206 by a miniature cable 208. A portion of cable 208 extends inside of the structural balloon. Although cable 208 is schematically illustrated as a straight cable in FIG. 7, it may be in a helical form similar to the structure of spring 256, and indeed may form a portion of spring 256 so as to permit axial expansion and contraction during deflation and inflation, respectively. Alternatively, cable 208 may extend within the bore 265 of the ablation device. Cable 208 continues to the proximal end of the catheter, through one of the lumens of the catheter. Each transducer element 204 of array 202 can be actuated in a manner similar to the manner of actuation of transducer element 86 of the imaging catheter (FIGS. 1-4), so that the radial position of the imaged region can be varied by varying the delay time between emission and reception of imaging pulses.

Numerous other variations and combinations of the features discussed above can be utilized. For example, the imaging array 202 may be mounted on other structures within the structural balloon as, for example, on elements on a reinforcing structure, such as on the periphery of engagement element or tube 60 (FIG. 2). Further, the imaging techniques discussed herein can be used in combination with other techniques such as the use of contrast medium as discussed in the aforementioned applications incorporated by reference herein. Also, the apparatus and methods according to the present invention can be applied to treatment of internal organs other than the heart.

INDUSTRIAL APPLICABILITY

The present invention can be applied in medical and veterinary treatment.

The invention claimed is:
1. An ablation catheter for ablating a region of a body while producing an image of the region, the ablation catheter comprising:
a catheter having a proximal end and a distal end and a central longitudinal axis, and an ablation device mounted to said catheter adjacent said distal end thereof, said ablation device having an expanded condition and a collapsed condition, said ablation device in said expanded condition being configured to apply ablation energy to an annular ablation region encircling said center longitudinal axis and located distally of the distal end of the catheter, the ablation device comprising:
a therapeutic ultrasound transducer, a structural balloon and a reflector balloon, the structural balloon and the reflector balloon arranged longitudinally adjacent to one another along the central longitudinal axis, the structural balloon and the reflector balloon having a common wall between them configured to direct ultrasound waves emitted by the therapeutic ultrasound transducer to the annular ablation region;
an ultrasonic imaging probe including an imaging transducer comprising a plurality of elements positioned to completely encircle the central longitudinal axis of the catheter, said ultrasonic imaging probe being adapted to image tissue structures in the annular ablation region encircling said center longitudinal axis and located distally of the distal end of the catheter, to receive return waves reflected by the reflector balloon to generate a ring-shaped image from the plurality of elements in the ultrasonic imaging probe, the ring-shaped image corresponding to the annular ablation region encircling said center longitudinal axis and located distally of the distal end of the catheter; and
an ultrasonic actuator configured to be selectively operated to actuate the therapeutic ultrasound transducer in a pulse mode, and an imaging receiver arranged to acquire signals from the image transducer, wherein the ultrasonic actuator is linked to the imaging receiver so that the imaging receiver is configured to receive signals from the imaging transducer within selected receive intervals commencing at a predetermined delay time after termination of a pulse from actuator.

2. The ablation catheter as claimed in claim 1 wherein said ablation device comprises a bore and said catheter has a port distal to said ablation device, wherein the ultrasonic imaging probe is configured to axially move through the bore and out of the port to acquire an image in a range of axial positions around the annular ablation region.

3. The ablation catheter as claimed in claim 2 wherein said ultrasonic imaging probe is positionable in an extended position in which said ultrasonic imaging probe projects out through said port so that said imaging transducer is disposed for imaging distal to said ablation device.

4. The ablation catheter as claimed in claim 2 wherein said ablation device in said expanded condition has an axis extending proximally and distally, said ablation device in said expanded condition being configured to apply ablation energy in the annular ablation region encircling said axis and located distally of the distal end of the catheter.

5. The ablation catheter as claimed in claim 4 wherein said imaging transducer is rotatable about said central longitudinal axis.

6. The ablation catheter as claimed in claim 5, wherein said ultrasonic imaging probe is movable to an interior operating position in which said at least one imaging transducer is disposed inside of said ablation device, said ultrasonic imaging probe being configured to image tissue in an ablation region surrounding said ablation device when said ultrasonic imaging probe is in said interior operating position.

7. The ablation catheter as claimed in claim 4 wherein said ablation device includes a balloon structure surrounding said axis.

8. The ablation catheter as claimed in claim 7 wherein said balloon structure includes an interior structure extending through said balloon structure, at least a portion of said interior structure being substantially transparent to ultrasonic waves.

9. The ablation catheter as claimed in claim 8 wherein said interior structure includes one or more engagement elements for reinforcing said balloon structure, at least one of said engagement elements being substantially transparent to ultrasonic energy.

10. The ablation catheter as claimed in claim 8 wherein said interior structure includes a spring adapted to elongate said balloon structure during deflation of said balloon structure, and wherein said spring is substantially transparent to ultrasonic energy.

11. The ablation catheter as claimed in claim 1 further comprising an indicator configured to gauge the axial position of the ultrasonic imaging probe.

12. The ablation catheter as claimed in claim 11, wherein the indicator further comprises marks or gradations on a proximal end of the ultrasonic imaging probe.

13. The ablation catheter as claimed in claim 11, wherein the indicator further comprises mechanical interconnections between the ultrasonic imaging probe as the catheter.

14. The ablation catheter as claimed in claim 11, wherein the indicator further comprises an electrical position sensing device.

\* \* \* \* \*